(12) United States Patent
Swain et al.

(10) Patent No.: US 8,323,023 B2
(45) Date of Patent: Dec. 4, 2012

(54) ORTHODONTIC KIT AND METHODS FOR SAME

(75) Inventors: Ryan B. Swain, Scottsville, NY (US); Merrit N. Jacobs, Fairport, NY (US)

(73) Assignee: Six Month Smiles, Inc., Scottsville, NY (US)

( * ) Notice: Subject to any disclaimer, the term of this patent is extended or adjusted under 35 U.S.C. 154(b) by 0 days.

(21) Appl. No.: 13/323,667

(22) Filed: Dec. 12, 2011

(65) Prior Publication Data

US 2012/0082951 A1 Apr. 5, 2012

Related U.S. Application Data

(62) Division of application No. 12/038,752, filed on Feb. 27, 2008, now abandoned.

(51) Int. Cl.
*A61C 5/00* (2006.01)

(52) U.S. Cl. ......................................................... 433/215

(58) Field of Classification Search .................. 433/2, 3, 433/24, 20, 49, 77, 79, 215; 206/63.5
See application file for complete search history.

(56) References Cited

U.S. PATENT DOCUMENTS

| | | | |
|---|---|---|---|
| 3,745,653 A * | 7/1973 | Cohl | ............................... 433/24 |
| 4,204,325 A | 5/1980 | Kaelble | |
| 4,701,129 A | 10/1987 | Hazard | |
| 4,731,018 A * | 3/1988 | Adell | ............................ 433/20 |
| 4,801,528 A | 1/1989 | Bennett | |
| 4,900,251 A | 2/1990 | Andreasen | |
| 4,978,007 A | 12/1990 | Jacobs | |
| 5,015,180 A | 5/1991 | Randklev | |
| 5,172,809 A | 12/1992 | Jacobs | |
| 5,172,810 A | 12/1992 | Brewer | |
| 5,183,403 A | 2/1993 | Masuhara | |
| 5,279,800 A | 1/1994 | Berry | |
| 5,348,154 A | 9/1994 | Jacobs | |
| 5,368,161 A | 11/1994 | Plais | |
| 5,484,283 A | 1/1996 | Franetzki | |
| 5,542,844 A | 8/1996 | Perret, Jr. | |
| 5,697,780 A | 12/1997 | Tuneberg | |
| 6,186,790 B1 | 2/2001 | Karmaker | |
| 6,312,258 B1 * | 11/2001 | Ashman | ........................ 433/172 |
| 6,315,553 B1 * | 11/2001 | Sachdeva et al. | ............... 433/24 |
| 6,423,550 B1 | 7/2002 | Jenkins | |
| 6,648,638 B2 | 11/2003 | Castro | |
| 6,682,344 B1 | 1/2004 | Stockstill | |
| 6,818,682 B2 | 11/2004 | Falsafi | |
| 7,039,628 B2 | 5/2006 | Logan | |
| 7,179,083 B2 | 2/2007 | Zanghellini | |
| 7,226,287 B2 | 6/2007 | Abels | |
| 2003/0225594 A1 | 12/2003 | Bergersen | |
| 2004/0157184 A1 | 8/2004 | Reising | |

(Continued)

OTHER PUBLICATIONS

International Search Report issued in related PCT/US2009/033048.

*Primary Examiner* — Sunil K Singh
(74) *Attorney, Agent, or Firm* — Jeffer Mangels Butler & Mitchell LLP

(57) ABSTRACT

A method for providing orthodontic therapy. The method includes the steps of providing a kit that includes an enclosure and tools and components for providing orthodontic therapy using braces to a single patient, applying the braces to the single patient's teeth using the tools, placing the tools back into the kit, storing the kit, and reusing the kit at all of the single patient's subsequent visits during the term of the orthodontic therapy.

13 Claims, 1 Drawing Sheet

U.S. PATENT DOCUMENTS

| | | |
|---|---|---|
| 2005/0016884 A1 | 1/2005 | Stout |
| 2005/0130096 A1 | 6/2005 | Stout |
| 2006/0057533 A1 | 3/2006 | McGann |
| 2006/0105287 A1 | 5/2006 | Wilburn |
| 2006/0127834 A1* | 6/2006 | Szwajkowski et al. ........... 433/2 |
| 2006/0134580 A1* | 6/2006 | Raby et al. ................... 433/213 |
| 2007/0111153 A1 | 5/2007 | Abels |
| 2008/0213724 A1 | 9/2008 | Erdrich |

* cited by examiner

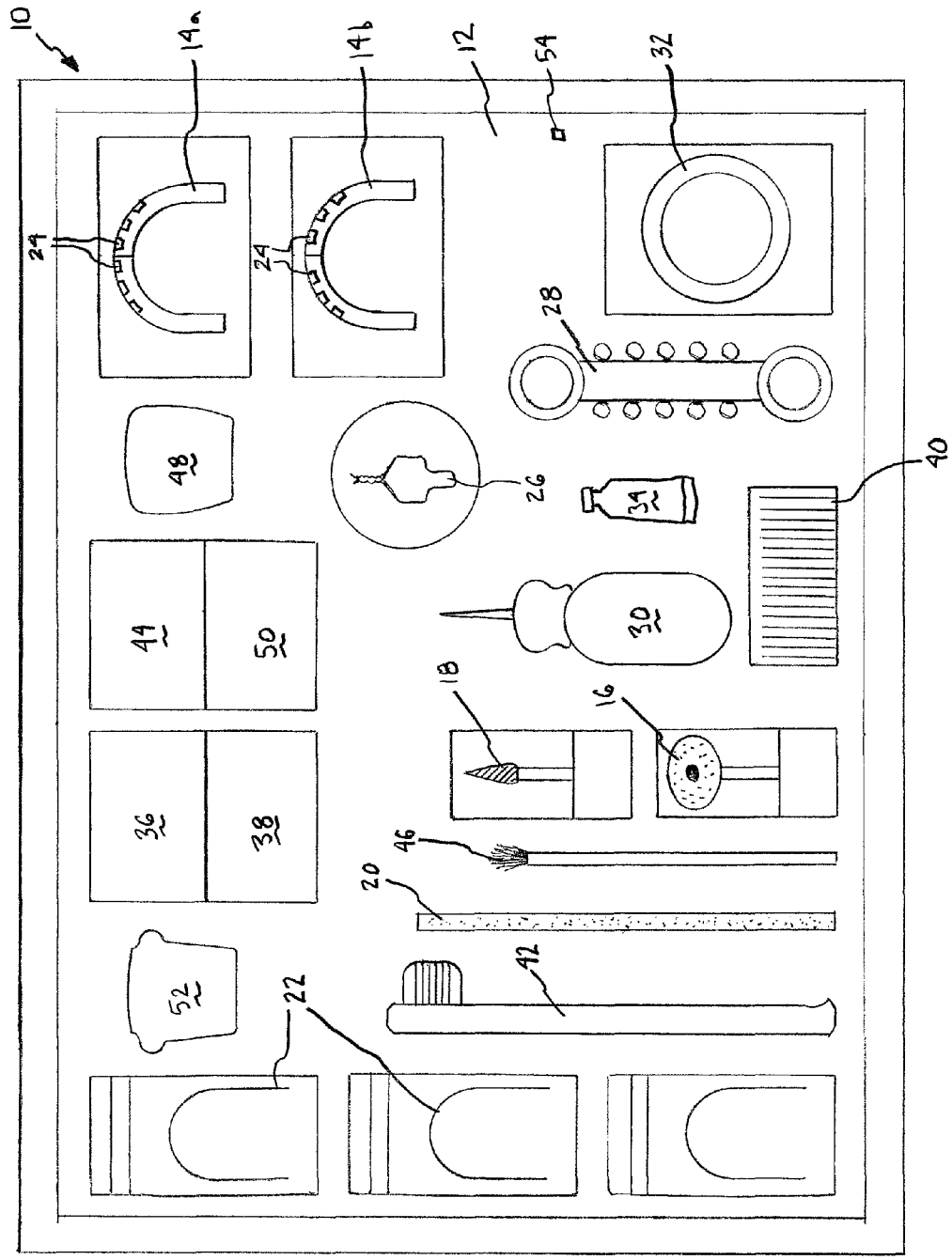

ORTHODONTIC KIT AND METHODS FOR SAME

CROSS REFERENCE TO RELATED APPLICATIONS

This application is a divisional of U.S. patent application Ser. No. 12/038,752, filed Feb. 27, 2008, the entirety of which is incorporated herein by reference.

FIELD OF THE INVENTION

The present invention relates generally to orthodontic kits and, more particularly, to orthodontic kits and methods for using same.

BACKGROUND OF THE INVENTION

Dentists performing orthodontics use a number of different tools and components to apply and adhere orthodontic brackets to teeth, prepare the teeth for the brackets and then attach wires and other tensioning devices to move the teeth.

Some dentists use indirect bonding trays to conveniently and accurately position all of the braces on the teeth. The bonding tray is made on a model of a patient's teeth and the brackets are included within the tray. These custom trays are then used to effectively bond the braces to the patient's teeth.

One issue with the current bracket attachment system is that bonding trays are made by independent orthodontic labs and the braces are made by separate orthodontic suppliers. The dentist typically inventories the brackets, and, after making the mold of the patient's teeth, pulls the desired brackets from his/her inventory and sends them, along with the models/molds of the patient's teeth, to the orthodontic lab. The lab then makes the bonding trays with the brackets (sent by the dentist) included therein and sends them back to the dentist.

After receipt of the indirect bonding trays, the dentist then uses a number of tools and components to place the braces (including the brackets) on the patients teeth. For example, during the procedure, the dentist may use a disc for enamel reproximation, a diamond bur for enamel reproximation, a diamond strip for enamel reproximation, orthodontic wires, metal and rubber ligature ties, bonding adhesive resin, cheek retractors and orthodontic cement among other tools and components. The current protocol is to purchase many of these tools and components from multiple suppliers. In addition to the time expended ordering components from multiple suppliers, many of the tools or components may not match the requirements of the particular patient's teeth. Also, many of the tools or components, such as the diamond disc, strip and bur require hot sterilization if they are to be used on multiple patients. Due to the high temperature and pressure, the hot sterilization damages and/or degrades the functionality of these tools over time. Other tools, for example the cheek retractor, are typically disposed of after a single visit to the office by a patient.

The need for the dentist to inventory supplies, such as wires, brackets, metal and rubber ligature ties, bonding adhesive resin, cheek retractors and orthodontic cement, as well as the need to sterilize and dispose of other components is time consuming, ineffective, costly and a hassle for the dentist. This puts a lot of responsibility on the dentist and it also increases the risk that the patient will be inconvenienced if there is a problem with inventory control or shipping.

Accordingly, a need exists for a solution to the problems discussed above.

SUMMARY OF THE PREFERRED EMBODIMENTS

In accordance with a first aspect of the present invention, there is provided a method for providing orthodontic therapy. The method includes the steps of providing a kit that includes an enclosure and tools and components for providing orthodontic therapy using braces to a single patient, applying the braces to the single patient's teeth using the tools, placing the tools back into the kit, storing the kit, and reusing the kit at all of the single patient's subsequent visits during the term of the orthodontic therapy. In a preferred, embodiment, the tools in the kit are never hot sterilized during the term of the orthodontic therapy.

In accordance with another aspect of the present invention, there is provided a kit for a dental patient that includes an enclosure and at least two of the following components: at least one bonding tray, a tool for enamel reproximation, an orthodontic wire, brackets, ligature ties, bonding adhesive, at least one cheek retractor, orthodontic cement, a thank you card to give to the patient, and a treatment plan. In preferred embodiment, the treatment plan is developed by a third party, not the patient's dental professional, specifically for the patient, the orthodontic wire and brackets are colored to match the patient's teeth, and the kit includes a system for associating the kit, the enclosure and at least two of the components with the patient.

In accordance with another aspect of the present invention, there is provided a method performed by a patient's dental professional. The method includes the steps of making a copy of a patient's teeth, and sending the copy of the patient's teeth to a kit provider that assembles a kit comprising an enclosure, and at least two of the following components: at least one bonding tray, a tool for enamel reproximation, an orthodontic wire, brackets, ligature ties, bonding adhesive, at least one cheek retractor, orthodontic cement, a thank you card to give to the patient, and a treatment plan. The method also includes, receiving the assembled kit, applying braces to the patient's teeth using the components in the kit, placing at least some of the components back into the kit, storing the kit, and reusing the kit at the patient's subsequent visits. In a preferred embodiment, the components in the kit are never hot sterilized after being placed in the enclosure.

The present invention provides a kit wherein the process of making indirect bonding trays is consolidated with providing the brackets and other tools/components. Practitioner inventory costs are reduced by eliminating the need to stock brackets, wires, metal and rubber ligature ties, and reproximation disc, strips and burs, etc. Preparation time is reduced because tools do not need hot sterilization, which can degrade the effectiveness of the tools because they are maintained for the particular patient in a convenient and reusable storage box. The components become unique tools to be used only on that patient. The present invention also helps eliminate the risk of cross contamination between patients.

BRIEF DESCRIPTION OF THE DRAWINGS

The invention may be more readily understood by referring to the accompanying drawings in which:

FIG. 1 is a top plan view of an orthodontic kit with the top removed in accordance with a preferred embodiment of the present invention.

Like numerals refer to like parts throughout the several views of the drawings.

DETAILED DESCRIPTION OF THE PREFERRED EMBODIMENTS

Described herein are preferred embodiments of an orthodontic kit and methods for using the kit 10 and the components therein and/or providing the kit to an orthodontic practitioner. In a preferred embodiment, the kit 10 of the present invention allows the dentist to provide orthodontic therapy for a specific patient. The kit 10 preferably comprises a single container 12 adapted for use with a single patient. The container 12 can include orthodontic tools and components that are necessary during the entire time over which the orthodontic practitioner provides the orthodontic therapy to the patient (i.e., the entire time from the application to the removal of the braces). In another embodiment, the kit may only include the tools and components necessary for the application or installation of the braces.

These components include (but are not limited to) upper and lower indirect bonding trays 14a and 14b (referred to generally herein as indirect bonding trays 14), a disc 16 for enamel reproximation, a diamond bur 18 for enamel reproximation, a diamond strip 20 for enamel reproximation (referred to collectively as "tools for enamel reproximation"), orthodontic wires 22 (different sizes can be included in a single kit), brackets 24, metal and rubber ligature ties 26 and 28, bonding adhesive resin 30, cheek retractors 32, orthodontic cement 34, thank you card to give to patient 36, treatment plan by an orthodontic professional 38 (discussed below), tooth picks 40 (or the like), tooth brush 42, referral cards to give to patient 44, a brush for painting bonding adhesive on teeth 46, patient facial wipe 48, patient instructions 50, patient wax 52, brackets and/or wires that are specifically colored for the patient's teeth 22 and 24 (discussed below) and other tools and components typically used in orthodontic procedures.

The current invention is to provide a kit 10 where the bonding tray (s) 14 and brackets 24 are pre-assembled by the company that makes the bonding tray(s) 14 using brackets 24 that are selected from a number of possible designs based on an evaluation of what will work best for that patient. It will be understood that the practitioner may only use a single bonding tray 14 if only the top or bottom teeth are being worked on. However, in the exemplary embodiment described herein two bonding trays 14 are used. In other embodiments, more than two trays can be used.

As discussed above, currently, the practitioner typically inventories brackets and sends those selected for the particular patient with the molds or teeth models (referred to generally herein as "a copy of the patient's teeth") to the lab. It is not efficient or practical for a practitioner to have a large variety of brackets. However, the orthodontic/dental lab, manufacturing facility or the like (referred to herein as the "kit provider"), because of the volume necessary to provide kits and brackets to multiple practitioners, can easily maintain this inventory. It will be understood that the custom trays greatly reduce the labor required by the practitioner because all of the brackets are in one tray and can be placed simultaneously as opposed to directly bonding brackets one by one without using trays.

Assembling all of the required parts for that particular patient by the kit provider results in lower operating cost for the practitioner because the practitioner will no longer need to maintain an inventory of the many parts required for this procedure. The bonding trays 14 (at least one tray for the upper teeth 14a and/or at least one tray for the lower teeth 14b) are customized for each specific patient because the kit provider gets to select the most appropriate components for this patient.

In use, the patient (referred to herein as "Patient A") visits the practitioner's office and the practitioner makes a mold of the patient's teeth. The practitioner then sends the mold and/or a model of the patient's teeth made from the mold to the kit provider. The kit provider then selects the brackets 24 for Patient A (based on the practitioner's request) from its inventory and prepares the custom bonding trays 14 for Patient A. The kit provider then places the trays 14 in a container 12 and assembles the kit 10 by collecting the remainder of the tools necessary for the orthodontic therapy of Patient A and ships the kit 10 to the practitioner.

Accordingly, the practitioner preferably receives a custom kit 10 made specifically for Patient A that contains bonding trays 14 made from the model of Patient A's teeth, which already contain the brackets 24 therein positioned properly for application to Patient A's teeth, along with a plurality of other components and tools, as listed above (some or all of the components and tools listed above can be included in the kit 10).

After Patient A visits the practitioner's office again, the practitioner applies the brackets 24 and the remainder of the components (commonly referred to collectively as "braces") to Patient A's teeth and uses various other tools from the kit 10 as desired. After the application process, the practitioner then places the tools, such as the diamond bur 18, strips 20 and disc 16, cheek retractor(s) 32, extra wires 22, ligatures 26 and 28, etc. back into the container 12 for use during Patient A's subsequent visits. The tools may be spray cleaned or the like, but none of them have to be hot sterilized or discarded because the only patient they will be used with is Patient A. However, they can be hot sterilized, if desired. The practitioner then stores the kit 10 as desired until it is needed for Patient A's next visit. Over the course of the orthodontic therapy to Patient A, the kit 10 is used each time Patient A visits the practitioner's office.

In one preferred embodiment, the kit 10 includes a treatment plan 38 by a professional/expert that is employed by/consults for or is otherwise retained by the kit provider. In this embodiment, the expert reviews the patient's teeth model/mold and develops a treatment plan based on his/her expertise. For example, the treatment plan 38 may include tips for which wires to start with, which teeth may need special attention, potential pitfalls to avoid (possibly referring to specific teeth), potential problems that could arise with this patient's bite, etc.

In another preferred embodiment, the kit 10 can include brackets 24 and/or wires 22 that are specifically colored for the patient's teeth. In this embodiment, at the time the practitioner takes the mold of the patient's teeth he/she can also use a shade tab or the like to determine the exact color of the patient's teeth. In a specific embodiment, the shade tab may be provided by the kit provider. The practitioner can then order from the kit provider brackets 24 and wires 22 that are colored to match the shade or color of the patient's teeth. These colored brackets and/or wires are then included in the kit 10.

In this embodiment, the kit provider may have the ability to coat and/or manufacture the brackets 24 and wires 22 to match the colors/shades ordered by the practitioner.

In another preferred embodiment, to provide even more assurance that the patient and components are matched, the kit can include a system for marking or coding the storage box/container 12 and all of the components, tools therein to assure that the parts are associated with or only used on the correct patient.

One method for doing this is to use RFID (radio frequency identification) tags on all of the components in the kit. The use of RFID technology is well known. Accordingly, a description of the technology and how it works will be omitted. All of the RFID tags 54 (only one tag is shown in FIG. 1 on the container 12, however, it will be understood that an RFID tag 54 would be included on most or all of the components therein) correspond to one another and provide a way to identify all of the components as belonging to or being associated with that kit and that patient. A corresponding RFID tag 54 can also be placed on the patient's chart. In performing any procedures on the patient, whether it be putting the braces on, adjusting the braces, etc., an RFID reader at the dental chair will then assure that all of the parts used in the procedure are associated with the current patient. RFID identification of dental components and patient data (x-rays, patient charts, for example) linked to the patients chart can be used in any dental specialty or in general dentistry. RFID technology is advantageously used to assure that all the components and information are correctly linked to the correct patient. This saves time, reduces the potential for error and allows the kit to be used with that patient throughout the period that he/she is fitted with the braces.

In another embodiment, to associate the components with that patient, a patient number can be associated with or placed on all of the components (chart, x-rays, etc.). For example, this can be done by placing numbered/lettered labels, stickers on the components, placing barcode readable placards/labels, etc. on the components or otherwise encoding the components. With this done, even if the items become separated from the primary storage box 12, they can still be identified properly.

In general, the kit 10 reduces in-chair labor, preparation labor time and inventory costs. It consolidates the process of making the bonding trays 14 with providing the brackets 24. Inventory costs are reduced by eliminating the need to stock brackets, wires, metal and rubber ligature ties, and reproximation disc, strips and burs. Preparation time is reduced because tools do not need hot sterilization, which can degrade the effectiveness of the instruments. In other cases, the bonding tray 14 can be used again if the patient knocks off a bracket 24. So, it is advantageous to keep the bonding tray (s) 14 in the kit 10.

The embodiments described above are exemplary embodiments of the present invention. Those skilled in the art may now make numerous uses of, and departures from, the above-described embodiments without departing from the inventive concepts disclosed herein. Accordingly, the present invention is to be defined solely by the scope of the following claims.

What is claimed is:

1. A method performed by a patient's dental professional comprising the steps of:
   a. making a copy of a patient's teeth,
   b. sending the copy of the patient's teeth to a kit provider, wherein the kit provider assembles a kit comprising an enclosure and at least two of the following components:
      i. at least one bonding tray,
      ii. a tool for enamel reproximation,
      iii. an orthodontic wire,
      iv. brackets,
      v. ligature ties,
      vi. bonding adhesive, and
      vii. at least one cheek retractor,
   c. receiving the assembled kit,
   d. applying braces to the patient's teeth using the components in the kit,
   e. placing at least some of the components back into the kit,
   f. storing the kit, and
   g. reusing at least one of the components from the kit at the patient's subsequent visits, wherein the components in the kit are never hot sterilized after being placed in the enclosure; and wherein the components are reused without being hot sterilized.

2. The method of claim 1 wherein the kit includes a patient treatment plan written specifically for the patient.

3. The method of claim 2 wherein the patient treatment plan was written by a third party who is not the patient's dental professional.

4. The method of claim 3 wherein the kit includes a patient identifier for associating the kit with the patient.

5. The method of claim 4 wherein the patient identifier is a barcode.

6. The method of claim 1 wherein the tool for enamel reproximation is a diamond bur, a diamond disc or a diamond strip.

7. The method of claim 1 wherein the kit includes at least first and second orthodontic wires, and wherein the first orthodontic wire is used at the patient's initial visit where the braces are applied, and wherein at a subsequent visit the first orthodontic wire is replaced with the second orthodontic wire.

8. A method comprising the steps of:
   a. receiving a kit that includes an enclosure and tools and components for providing orthodontic therapy using braces to a single patient,
   b. applying the braces to the single patient's teeth using the tools,
   c. placing the tools back into the kit,
   d. storing the kit, and
   e. reusing at least one of the tools or components from the kit at all of the single patient's subsequent visits during the term of the orthodontic therapy, wherein the components and tools in the kit are never hot sterilized after being placed in the enclosure; and wherein the components are reused without being hot sterilized.

9. The method of claim 8 wherein the kit includes indirect bonding trays.

10. The method of claim 9 wherein the kit includes a patient treatment plan written specifically for the single patient.

11. The method of claim 10 wherein the patient treatment plan was written by a third party who is not the patient's dental professional.

12. The method of claim 8 wherein the kit includes a patient identifier for associating the kit with the patient.

13. The method of claim 12 wherein the patient identifier is a barcode.

* * * * *